United States Patent [19]

Paludetto et al.

[11] Patent Number: 5,563,299
[45] Date of Patent: Oct. 8, 1996

[54] INTEGRATED PROCESS FOR THE SIMULTANEOUS PRODUCTION OF ALKYL TERT-BUTYL ETHERS AND 1-BUTENE

[75] Inventors: Renato Paludetto, Pioltello; Gianni Donati, Rho; Alfredo Orsi, Corsico; Gianni Pandolfi, Novara; Roberto Trotta, Milan; Maura Brianti, Busto Arsizio, all of Italy

[73] Assignees: Enichem S.p.A; Snamprogetti S.p.A., both of Milan, Italy

[21] Appl. No.: 383,317

[22] Filed: Feb. 3, 1995

[30] Foreign Application Priority Data

Feb. 11, 1994 [IT] Italy ................................. MI94A0244
Nov. 24, 1994 [IT] Italy ................................. MI94A2385

[51] Int. Cl.$^6$ ....................................................... C07C 41/06
[52] U.S. Cl. ........................................................... 568/697
[58] Field of Search ............................................... 568/697

[56] References Cited

U.S. PATENT DOCUMENTS 4,581,474  4/1986  Hutson, Jr. et al. .
5,300,696  4/1994  Luebke et al. ............................ 568/697
5,338,889  8/1994  Vora et al. .
5,382,707  1/1995  Rubin et al. ............................. 568/697

FOREIGN PATENT DOCUMENTS 0474188  3/1992  European Pat. Off. .

Primary Examiner—Gary Geist
Assistant Examiner—Dwayne C. Jones
Attorney, Agent, or Firm—Oblon, Spivak, McClelland, Maier & Neustadt, P.C.

[57] ABSTRACT

An integrated process for the simultaneous production of alkyl tert-butyl ethers and 1-butene, comprising feeding a $C_4$ hydrocarbon stream to an etherification unit and recycling the remaining stream to the same unit after possible separation of the 1-butene and treatment in an isomerization section to convert the remaining butenes into isobutene, a molecular sieve separation unit operating with the hydrocarbons in the vapour phase being incorporated into the cycle.

17 Claims, 3 Drawing Sheets

INTEGRATED PROCESS FOR THE SIMULTANEOUS PRODUCTION OF ALKYL TERT-BUTYL ETHERS AND 1-BUTENE

BACKGROUND OF THE INVENTION

1. Field of the Invention

This invention relates to an integrated process for producing alkyl tert-butyl ethers and possibly 1-butene.

More particularly, the invention relates to an integrated process for producing methyl tert-butyl ether (MTBE) or ethyl tert-butyl ether (ETBE) and possibly 1-butene.

Still more particularly, the invention relates to maximizing the use of the butene fraction in an integrated cycle for producing MTBE or ETBE and possibly 1-butene.

2. Description of the Prior Art

Alkyl tert-butyl ether production processes are known in the art, consisting of reacting the isobutene contained in $C_4$ hydrocarbon streams of different origin, in particular in streams originating from steam cracking, catalytic cracking or isobutane dehydrogenation plants, with an alcohol preferably chosen from methanol and ethanol. U.S. Pat. Nos. 3,979,461, 4,039,590 and 4,071,567 describe for example certain MTBE processes in which the isobutene, contained in $C_4$ streams with may also include butadiene, is reacted with methanol in the presence of an acid ion exchange resin. Other MTBE synthesis processes are described in U.S. Pat. No. 4,475,005 and in published European patent application 470,655.

This known processes enable the isobutene to undergo virtually total conversion, leaving the other components practically unchanged to be recovered and upgraded.

British patent 2,121,407 and U.S. Pat. No. 4,513,153 for example describe an alkyl tert-butyl ether production process with an associated cycle for upgrading the residual components still present in the $C_4$ stream leaving the etherification reactor. In these patents the $C_4$ stream, after synthesis and separation from the tert-butyl ether, is fed to a skeleton isomerization unit for converting the 1-butene and cis and trans 2-butenes to isobutene, and recycled to the alkyl tert-butyl ether synthesis section.

Because of the fact that in such an integrated system an undesirable accumulation of inerts, represented essentially by saturated hydrocarbons such as n-butane and isobutane, takes place, a fractionation or extractive distillation section for the $C_4$ hydrocarbon feedstock is inserted between the etherification and isomerization sections to separate the saturated from the unsaturated hydrocarbons.

However the integrated alkyl tert-butyl ether process of the known art suffers from the drawbacks of having to operate a fractionation or an extractive distillation section, which inevitably significantly increases investment and production costs.

The current process alternative is simply to bleed off. However this method also has drawbacks in that together with the inerts, unsaturated hydrocarbons consisting essentially of 1- and 2- butenes, are also bled off. These butenes in the case of the integrated cycle, represent valuable materials to be upgraded by conversion into isobutene and then in to ethers. A further drawback, of no less importance, is the need to increase the inerts concentration in the cycle to reduce the butenes lost by bleeding, this resulting in increased investment and energy consumption.

A 1-butene recovery section can also be inserted into such a scheme. Processes are known in the art for recovering 1-butene from mixtures containing it. U.S. Pat. No. 4,718,986 for example describes a process for separating 1-butene contained in a $C_4$ stream using a distillation unit. In this patent, isobutane is separated as top product from a first column, otherwise it would contaminate the final 1-butene product recovered at high purity (>99%) as top product from a second distillation column. The isobutane quantity in the feedstock influences not only investment and energy consumption relating to the first column but also the overall butene yield in that it entrains consistent 1-butene quantities (on an average in an isobutane/1-butene ratio of $1/15$) within the overhead bleed of the first column.

Again in this case, the 1-butene is separated at the expense of significant losses of valuable material in the overhead bleed of the first distillation column, which are additional to those of the bottom bleed of the second distillation column.

SUMMARY OF THE INVENTION

The present applicant have now discovered a new integrated process for producing alkyl tert-butylethers and possibly 1-butene from essentially butadiene-free $C_4$ hydrocarbon streams which obviates the drawbacks of the know art. In this respect the present process provides total or partial separation of the inert hydrocarbons to be bled off by operating selective olefin adsorption on zeolites. The olefins adsorbed in this manner can be recovered by desorption and then fed either directly to a skeleton isomerization section or to a 1-butene separation unit.

In this second case the remaining hydrocarbon stream is then fed to the skeleton isomerization section. From this section the hydrocarbon stream is then recycled to the etherification unit. This result can be obtained if the molecular sieve separation is conducted with a vapour phase stream in that operating with a liquid phase stream leads to unsatisfactory results.

The present invention therefore provides an integrated process for producing alkyl tert-butyl ethers comprising:

a) feeding a $C_4$ hydrocarbon stream consisting essentially of isobutene, linear butenes and butanes and possible traces of butadiene, by virtue of the fact that it originates for example from a butadiene hydrogenation unit, to an alkyl tert-butyl ether synthesis section together with an aliphatic alcohol stream;

b) separating the ether produced and any unreacted alcohol from the hydrocarbon stream;

c) feeding the remaining hydrocarbons stream, or a fraction thereof, in the vapour phase to a molecular sieve separation section for separating the butanes from the butenes and recovering the butenes;

d) feeding the hydrocarbon stream containing the recovered butenes, together with the possible fraction not fed to stage c), to a skeleton isomerization section for converting the linear butenes to isobutene;

e) recycling the isomerized stream to the alkyl tert-butyl ether synthesis reactor after mixing with the $C_4$ hydrocarbon feedstock stream.

Alternatively the $C_4$ hydrocarbon stream can be practically free from isobutene by virtue of originating from an existing alkyl tert-butyl ether synthesis plant. In this case the $C_4$ stream is fed directly to the isomerization section and then to the etherification section.

After separation of the produced ether, the outgoing stream is fed to the saturated hydrocarbons separation unit, recycling the butenes fraction to the isomerization section.

A further integrated process for producing alkyl tert-butyl ethers can comprise:

a) feeding a $C_4$ hydrocarbon stream consisting essentially of isobutene, linear butenes and butanes and possible traces of butadiene, by virtue of the fact that it originates for example from a butadiene hydrogenation unit, to an alkyl tert-butyl ether synthesis section together with an aliphatic alcohol stream;

b) separating the ether produced and any unreacted alcohol from the hydrocarbon stream;

c) feeding the remaining hydrocarbon stream to a skeleton isomerization section for converting the linear butenes to isobutene;

d) feeding the isomerized hydrocarbon stream coming from c), or a fraction thereof, in the vapour phase to a molecular sieve separation section for separating the butanes from the butenes and recovering the butenes;

e) recycling the isomerized stream containing the recovered butenes, together with the possible fraction not fed to stage d), to the alkyl tert-butyl ether synthesis reactor after mixing with the $C_4$ hydrocarbon feedstock stream.

In this further form of the process of the present invention, the $C_4$ hydrocarbon stream can again be practically free from isobutene by virtue of originating from an existing alkyl tert-butyl ether synthesis plant. In this case the $C_4$ stream is fed directly to the isomerization section and then to the molecular sieve separation section.

In the case of an integrated process for simultaneously producing alkyl tert-butyl ethers and 1-butene, this process comprises:

a) feeding a fresh $C_4$ hydrocarbon feedstock stream, consisting essentially of isobutene, linear butenes and butanes, plus a recycle stream containing possible traces of butadiene, to an alkyl tert-butyl ether synthesis section together with an aliphatic alcohol stream;

b) separating the ether produced and any unreacted alcohol from the hydrocarbon stream;

c) feeding the remaining hydrocarbon stream, or a fraction thereof (first by-pass), in the vapour phase to a molecular sieve separation section for separating the paraffins (consisting essentially of butanes) from the butenes, recovering the butenes and bleeding off the paraffins;

d) feeding the thus treated hydrocarbon stream to a butadiene selective hydrogenation unit;

e) feeding the hydrocarbon stream from the butadiene hydrogenation unit, or a fraction thereof (second by-pass), to a 1-butene separation unit to obtain a 1-butene stream of purity exceeding 99%, a bleed stream consisting essentially of residual isobutane and 1-butene (isobutane stream) and a stream consisting essentially of 2-butenes, 1-butene and residual n-butane (butene stream);

f) feeding the butene stream of stage e) to a skeleton isomerization section for converting the linear butenes to isobutene;

g) feeding the isobutane stream of stage e) either to the molecular sieve separation section or directly to the isomerization section;

h) recycling the isomerized stream to the alkyl tert-butyl ether synthesis reactor after mixing with the $C_4$ hydrocarbon feedstock stream.

According to an alternative embodiment of the integrated process for simultaneously producing alkyl tert-butyl ethers and 1-butene according to the present invention, the $C_4$ hydrocarbon feed stream can contain traces of butadiene and be practically free from isobutene by virtue of originating for example from an existing alkyl tert-butyl ether synthesis plant. In this case the $C_4$ stream is fed directly upstream of the butadiene selective hydrogenation unit and downstream of the molecular sieve separation section.

According to a further alternative embodiment of the integrated process for simultaneously producing alkyl tert-butyl ethers and 1-butene, the butadiene selective hydrogenation unit can be positioned upstream of the molecular sieve separation section and also upstream of its by-pass. Again in this second alternative embodiment of the present process, the $C_4$ hydrocarbon stream can contain traces of butadiene and be practically free from isobutene. In this case the $C_4$ hydrocarbon stream is fed upstream of the selective hydrogenation unit and downstream of the etherification section.

BRIEF DESCRIPTION OF THE DRAWINGS

The Figures show various block schemes representing three embodiments of the invention (FIGS. 1, 2, 3 and 4) and one embodiment showing only the molecular sieve separation section (FIG. 5).

DESCRIPTION OF THE PREFERRED EMBODIMENTS

Figure 1:
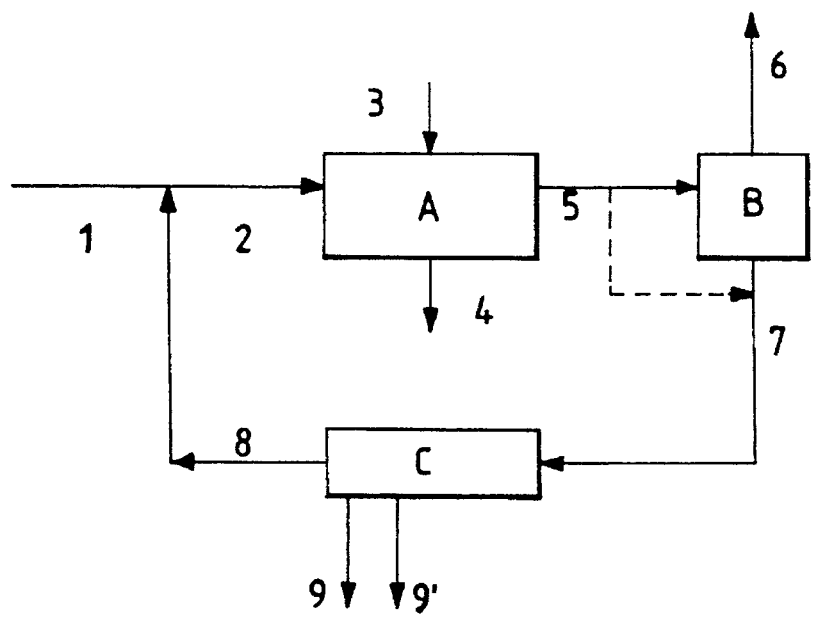

The $C_4$ hydrocarbon stream used in the process of the present invention consists of isobutane, isobutene, n-butane, 1-butene, trans or cis 2-butene and possibly small quantities of $C_3$ or $C_5$ hydrocarbons and is substantially free from butadiene by virtue of originating from a butadiene hydrogenation or removal unit. In particular, a $C_4$ stream can contain the following in addition to a small quantity of $C_3$ and $C_5$ for example between 0 and 5 wt %: 0.5–45 wt % of isobutane; 1–20 wt % of n-butane; 5–55 wt % of isobutene; the remainder to 100 being the linear butenes.

Any aliphatic alcohol can be used in the process of the present invention, although methyl and ethyl alcohol are preferred to produce methyl tert-butyl ether (MTBE) and ethyl tert-butyl ether (ETBE) respectively.

The etherification reaction is preferably conducted in the liquid phase in the presence of an acid catalyst. The operating conditions are conventional and are described in U.S. Pat. Nos. 3,979,461, 4,039,590 and 4,071,567, 4,447,653 and 4,465,870. As an alternative to traditional technology the ether can be synthesized by means of a column reactor, in accordance with the catalytic distillation principle described for example in U.S. Pat. No. 4,475,005 and in published European patent application 470,655.

The hydrogen stream originating from the etherification unit is fed to a separation section to recover the ether produced and any unreacted alcohol. The residual $C_4$ fraction is separated from the ether in a normal distillation column, from the bottom of which a product separates consisting essentially of ether. The $C_4$ hydrocarbons are recovered from the top of the column in azeotropic mixture with the unreacted alcohol. The alcohol is then removed by known methods, for example by extraction with water.

The residual $C_4$ fraction, free from ether and alcohol, or a fraction thereof exceeding 5 wt % of the total available stream, is fed to a molecular sieve separation section to eliminate the aliphatic hydrocarbon inerts consisting essentially of n-butane and isobutane.

Any zeolite molecular sieve selective towards the olefinic double bond can be used in the process of the present invention. For example, compounds can be used corresponding to those of general formula (I):

$$(Cat_{2/n}O)_x Me_2O_3 (SiO_2)_y \qquad (I)$$

where:

Cat represents a cation of valency "n" interchangeable with calcium (Ca), such as sodium, lithium, potassium, magnesium etc;

x is a number from 0.7 and 1.5;

Me represents boron or aluminium; and y is a number between 0.8 and 200, preferably between 1.3 and 4.

Preferred zeolites are those of X and Y type with a particle size of between 0.1 and 3 mm. These zeolites enable olefin/paraffin selectively ratios of between 3 and 12 to be obtained, selectivity being defined as:

$$S = \frac{\Gamma_o/P_o}{\Gamma_p/P_p}$$

where $\Gamma_o$ and $\Gamma_p$ are the adsorbed molar quantities of olefins (o) and paraffins (p) in equilibrium with their respective partial pressures $P_o$ and $P_p$ in the vapour.

The aliphatic hydrocarbons are separated in the vapour phase at a temperature between 20° and 180° C., preferably between 70° and 140° C., and a pressure between 1 and 10 bar absolute, preferably between 1 and 5. To ensure continuity of the process according to the present invention, it is preferred to use a system comprising at least two sections arranged in parallel so that while one section is adsorbing the other is desorbing. Desorption is achieved by eluting the olefins adsorbed onto the molecular sieves with a desorbing agent, for example aliphatic hydrocarbons such as pentane, hexane, heptane, octane etc., in the vapour phase followed by rectification of the mixture obtained to recover the olefins.

The process of the present invention enables an aliphatic hydrocarbon stream to be obtained which is practically free from olefins or with an olefin content of up to 5 wt %.

The olefinic stream leaving the molecular sieve separation section, consisting essentially of the residual butane fraction and of 1-butene and of cis and trans 2-butene, is fed to the isomerization section for converting the 1-butene and cis and trans 2-butene to isobutene.

In the case of an integrated process for simultaneously producing alkyl tert-butyl ethers and 1-butene, the olefinic stream leaving the molecular sieve separation section, consisting essentially of the residual butane fraction, 1-butene and cis and trans 2-butene, is fed to the section for the selective hydrogenation of the butadiene which may form in the subsequent skeleton isomerization section.

The butadiene-free hydrogenated $C_4$ stream is fed to the 1-butene separation section.

Given that during the butadiene hydrogenation $C_3$- light hydrocarbons can form, a removal section for such light hydrocarbons, for example by distillation, is inserted into the cycle preferably before the 1-butene separation section upstream of the second by-pass.

The 1-butene can be separated by known methods such as distillation, extractive distillation or adsorption on molecular sieves. Separation by distillation is preferred according to the present invention, generally effected with two distillation columns arranged in series. In a typical configuration, the isobutane (isobutane stream) still present in the feed stream is separated at the top of the first column, the top product in the second column being 1-butene with a purity exceeding 99%, the bottom product being a stream rich in residual n-butane, cis and trans 2-butene and traces of 1-butene (butene stream). The operating conditions are described in U.S. Pat. No. 4,718,986 and Canadian patent 1,232,919.

In an alternative configuration for separating the 1-butene by distillation, the butene stream is discharged from the bottom of the first column, the second column providing as bottom product high purity 1-butene, with isobutane (isobutene stream) discharged from the top.

In addition to isobutene, the isobutene stream contains a certain quantity of 1-butene and can hence be recycled to the molecular sieve separation section upstream or downstream of the by-pass, or alternatively to the isomerization section. In this second case it is possible not to include in the cycle the section for removing $C_3$- hydrocarbons formed during butadiene hydrogenation, as these latter are eliminated in the subsequent skeleton isomerization section.

The butene stream is fed to the isomerization section for converting the linear butenes to isobutene.

The isomerization reaction can be conducted for example by the process described in U.S. Pat. No. 4,038,337 using as catalyst a silicized alumina product described in U.S. Pat. Nos. 4,013,589 and 4,013,590, or using zeolite catalysts such as those described for example in published European patent applications 523,838 and 501,577.

At the exit of the isomerization section an isobutene-rich stream is obtained which can be recycled to alkyl tert-butyl ether synthesis. Any $C_3$- and $C_5$+ hydrocarbons formed in this stage are removed, for example by distillation.

The integrated process for producing alkyl tert-butyl ethers of the present invention can be better illustrated by reference to the block schemes of FIG. 1, 2, 3 and 4 which represent three embodiments thereof by way of non-limiting example, and to the block scheme of FIG. 5 which represents one exemplificative embodiment of only the molecular sieve separation section. With reference to FIG. 1, A, B and C represent respectively the alkyl tert-butyl ether synthesis section, the aliphatic hydrocarbon molecular sieve separation section and the skeleton isomerization section. The feed stream (2), consisting of the sum of the $C_4$ hydrocarbon fraction (1) and the recycle fraction (8) from the isomerization unit C, is fed to the synthesis section A together with the aliphatic alcohol (3). Having recovered the produced ether (4) by conventional systems not shown in the figure, the residual fraction (5) is fed totally or partially to the separation section B. If partial separation is used, part of said residual fraction by-passes the separation section B (dashed line).

The stream (7) from the separation section B, consisting essentially of 1-butene and cis and trans 2-butene plus residual butanes, enters the isomerization section C. From this the isobutene-rich stream (8) is extracted and recycled to the section A. Any $C_3$- or $C_5$+ hydrocarbons formed during isomerization are discharged via (9) and (9').

Figure 2:
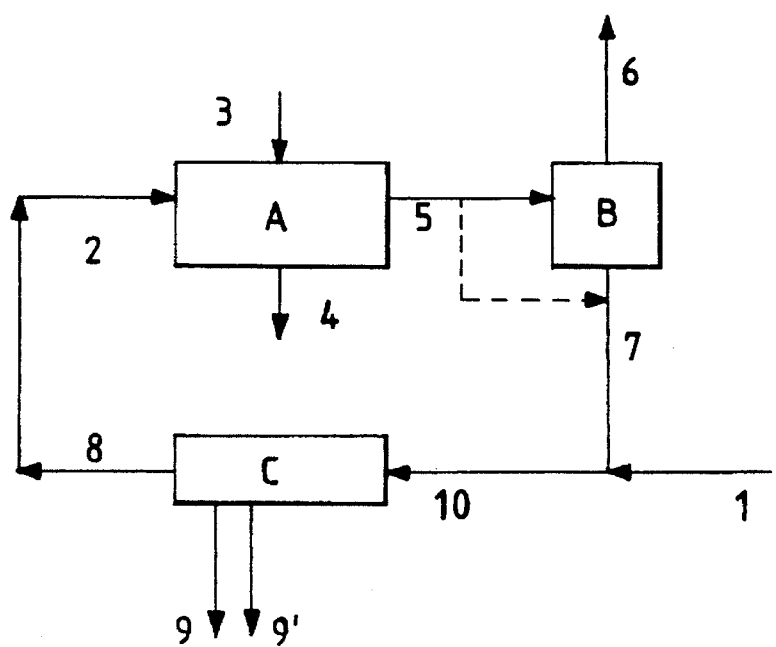

In FIG. 2 the hydrocarbon fraction (1) is practically free from isobutene by virtue of the fact that it originates for example from an existing alkyl tert-butyl ether synthesis plant. Consequently this stream is fed via line (10) directly to the isomerization section together with the stream (7) from the separation section.

Figure 3:
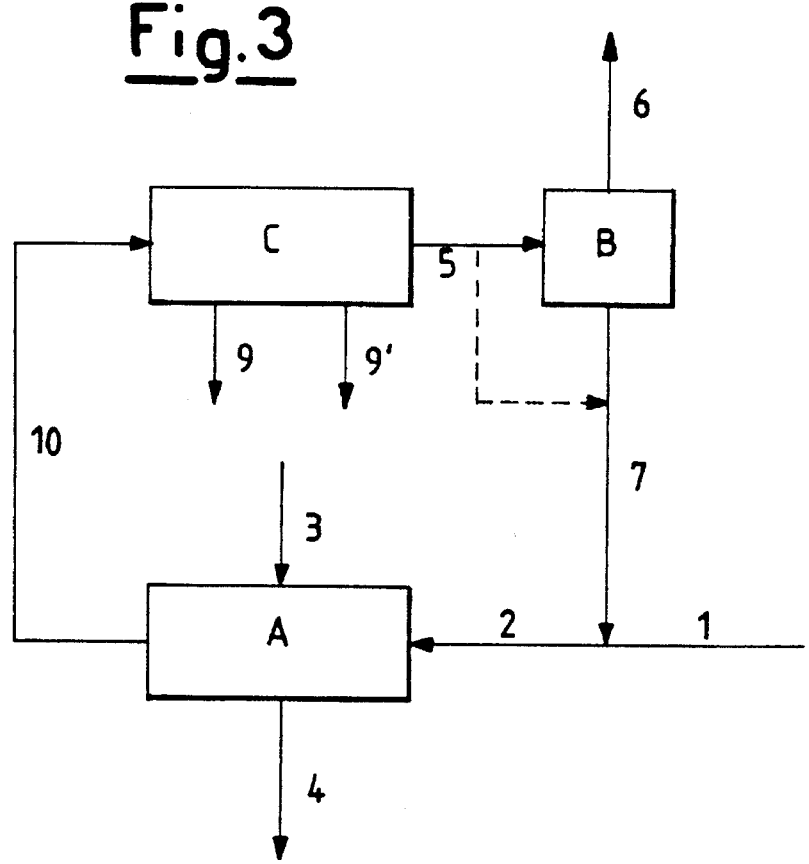

In FIG. 3 the separation section B is positioned after the isomerization section C.

Figure 4:
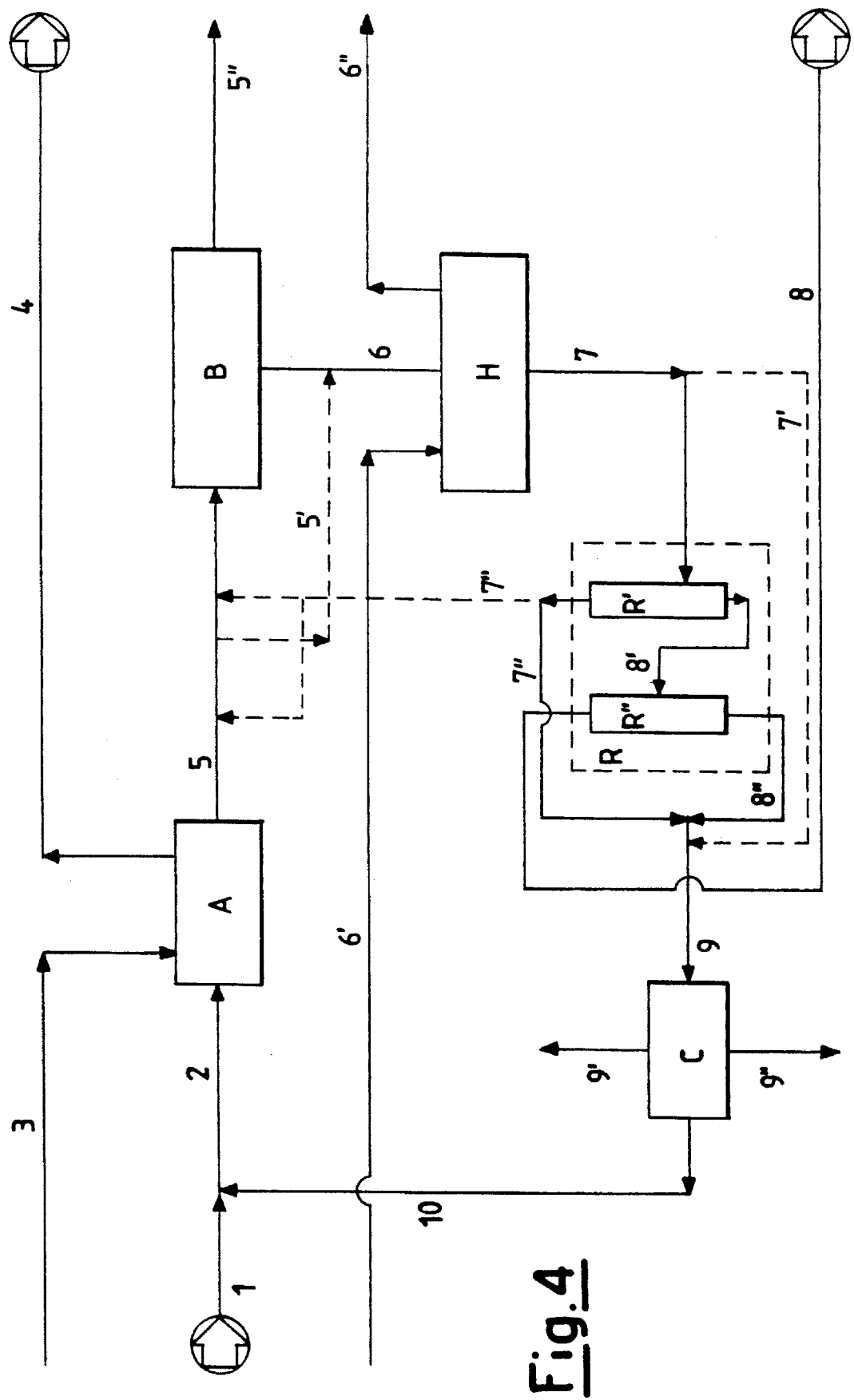

FIG. 4 shows a process scheme for simultaneously producing alkyl tert-butyl ethers and 1-butene. The blocks A, B, C, H and R represent respectively the alkyl tert-butyl ether synthesis section (A), the paraffin hydrocarbon molecular sieve separation section (B), the skeleton isomerization section (C), the hydrogenation section (H) and the 1-butene separation section (R). The feed stream (2), consisting of the sum of the fresh feedstock C₄ hydrocarbon stream (1) and the recycle stream (10) from the isomerization unit (C), is fed to the synthesis section (A) together with the aliphatic alcohol (3). Having recovered the produced ether (4) by conventional systems not shown in the figure, the residual fraction (5) is fed totally or partially to the molecular sieve separation section B. If partial separation is used, part of the fraction by-passes the separation section B (dashed line 5').

From the separation section B a stream (5") is obtained which consists essentially of butanes practically free from olefins and is discharged from the cycle, and a stream (6) consisting essentially of 1-butene and cis and trans 2-butene plus residual butanes. As this stream can contain butadiene, it is fed to the hydrogenation section (H) together with a hydrogen stream (6').

Two exit streams are obtained, namely an offgas stream (6") and a hydrogenated stream (7).

The hydrogenated stream (7) is fed totally or partially to the 1-butene separation section (R). If partial separation is used, part of said stream by-passes the separation section R (dashed line 7').

In this particular case the 1-butene separation section operates by distillation and comprises two distillation columns. The first (R'), fed with the stream (7), produces as top product a stream consisting essentially of isobutane and 1-butene (7") (isobutane stream). This stream can be recycled to the molecular sieve separation section B either upstream or downstream of the by-pass (5') or be fed directly to the isomerization section C.

The second column (R"), fed with the bottom product (8') from the column R', produces as top product 1-butene (8) with the required specification (purity exceeding 99%) and as bottom product a stream (8") which together with the possible streams (7') and/or (7") is fed to the isomerization section C via (9). The stream (10) which is rich in isobutene and contains possible traces of butadiene is extracted from this section and is recycled to the section A. Any C₃- and C₅+ hydrocarbons formed during isomerization or which have entered the cycle with the feedstock (1) are discharged via (9') and (9").

Given that during the selective butadiene hydrogenation C₃- light hydrocarbons can form, the process scheme can comprise a removal unit, for example a distillation unit, for eliminating these compounds. The distillation unit, not shown in the figure, can be positioned directly downstream of the hydrogenation section and upstream of the 1-butene separation section, before the by-pass, ie in the line (7") before it joins the stream (5).

In an alternative configuration of the 1-butene distillation recovery section, the butene stream (8") is taken from the bottom of the first column R' whereas the stream (8) is taken from the bottom of the second column R", the isobutane stream (7") being taken from its top.

Figure 5:
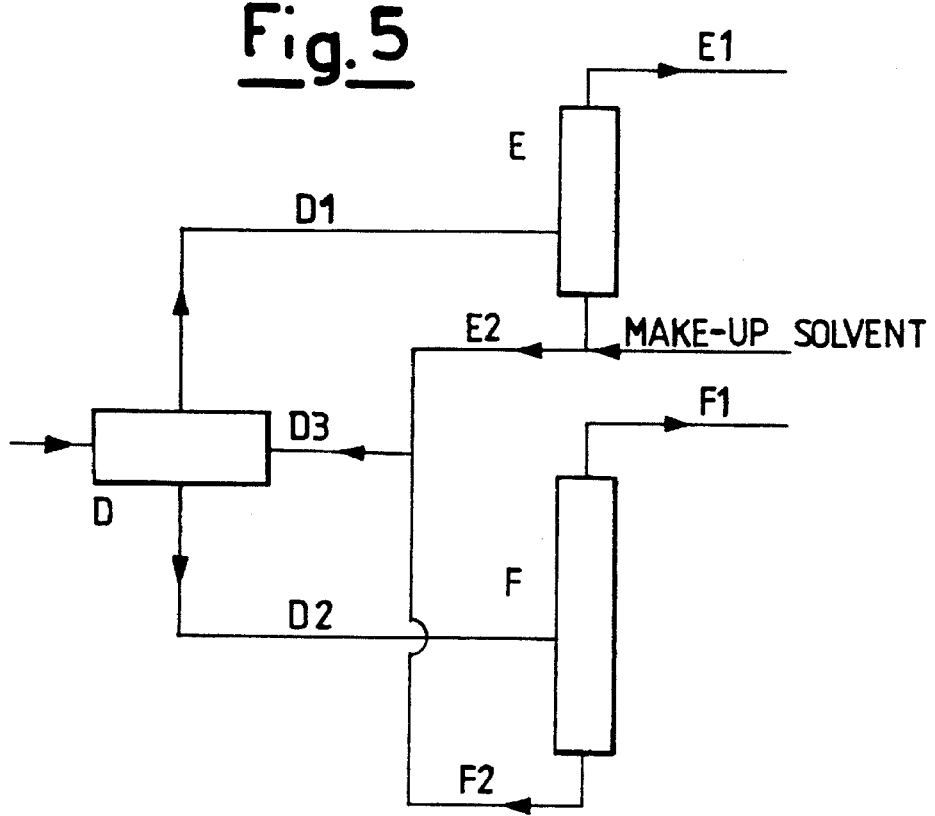

The separation section B comprises an adsorption/desorption unit D and two distillation columns E and F (FIG. 5).

For continuous operation two units D can be provided operating alternatively, one in the adsorption phase and the other in the desorption one.

Two streams D1 and D2 are recovered from the unit D.

The stream D1 is recovered during adsorption practically free from olefins and is fed to the distillation column E for recovery of the recycled desorbent E2 from the butane bleed fraction E1.

The olefinic fraction D2 is recovered during desorption and is fed to the distillation column F for recovering the butene fraction F1 (returned to the cycle) from the desorbent F2 which is recycled.

In all the configuration shown in FIGS. 1, 2, 3 and 4, the process of the present invention enables a practically olefin-free paraffinic stream to be bled off in an integrated process for producing alkyl tert-butyl ethers and possibly 1-butene. It therefore allows virtually total utilization of the available olefins, hence maximizing tert-butyl alkyl ether production. It also enables the paraffin concentration in the cycle to be reduced, hence reducing investment and energy consumption.

Some non-limiting illustrative examples are given hereinafter to provide a better understanding of the invention and its implementation.

EXAMPLE 1

With reference to the scheme of FIG. 1 and to the relative Table 1 showing the process quantities for a capacity of 1000 kg/a, a reactor for MTBE production is fed with a C₄ hydrocarbon stream at a rate of 99.6 g/h having the following composition:

|  | wt % |
|---|---|
| C3 | 0.10 |
| i-butene | 24.26 |
| n-butenes | 70.18 |
| butanes | 5.46 | in combination with the recycle stream (8) at a rate of 217.3 g/h.

45.4 g/h of methanol (line 3) are also fed to the reactor.

The MTBE (4) production is 125 g/h, equivalent to an isobutene conversion of 99.5%.

237.3 g/h of residual C₄ fraction containing about 16 wt % of aliphatic hydrocarbons are discharged from the synthesis section A via (5). About 75% of this fraction is by-passed, the remainder being fed to the molecular sieve separation section operating at 130° C. and 4 bar pressure. 100 cc of zeolite X in the form of 1/16" extruded pellets are used as adsorbent, n-hexane in the vapour phase (about 120 g/h) being used as desorbent for the adsorbed olefins. After separating the desorbent by distillation, a stream (6) consisting essentially of 4.7 g/h of aliphatic hydrocarbons with a paraffin content of about 96.7% is bled off. In stream (7) the aliphatic hydrocarbon content is reduced to 14.2 wt % after separating the desorbent by distillation.

The stream (7) is fed to the isomerization section C in which the n-butenes are converted to isobutene and other by-products generally falling within the C₃- and C₅+ categories. These by-products are eliminated (streams 9 and 9') and the resultant fraction (8) is recycled to the MTBE synthesis section.

TABLE 1

MATERIAL BALANCE (g/h)

|  | 1 | 2 | 3 | 4 | 5 | 6 | 7 | 8 | 9 | 9' |
|---|---|---|---|---|---|---|---|---|---|---|
| C3− | 0.1 | 0.7 |  |  | 0.7 | 0.0 | 0.7 | 0.6 | 2.6 | 0.0 |
| isobutene | 24.2 | 79.9 |  |  | 0.4 | 0.0 | 0.4 | 55.8 | 0.4 | 0.2 |
| n-butene | 69.9 | 195.8 |  |  | 195.8 | 0.2 | 195.7 | 126.0 | 0.3 | 2.0 |
| butanes | 5.4 | 37.6 |  |  | 37.6 | 4.6 | 33.1 | 32.2 | 0.3 | 1.1 |
| C5+ | 0.0 | 2.7 |  |  | 2.7 | 0.0 | 2.7 | 2.7 | 0.0 | 8.5 |
| methanol | 0.0 | 0.0 | 45.4 |  |  |  |  |  |  |  |
| MTBE | 0.0 | 0.0 |  | 125.0 |  |  |  |  |  |  |
| TOTAL | 99.6 | 316.9 | 45.4 | 125.0 | 237.3 | 4.7 | 232.6 | 217.3 | 3.5 | 11.8 |
| Tot. OLEF | 94.0 | 275.8 | 0.0 | 0.0 | 196.1 | 0.2 | 196.1 | 181.7 | 0.7 | 2.2 |

|  | wt % | wt % | wt % | wt % | wt % | wt % | wt % | wt % | wt % | wt % |
|---|---|---|---|---|---|---|---|---|---|---|
| C3− | 0.10 | 0.23 | 0.00 | 0.00 | 0.31 | 0.01 | 0.32 | 1.38 | 72.26 | 0.00 |
| isobutene | 24.26 | 25.22 | 0.00 | 0.00 | 0.17 | 0.01 | 0.17 | 24.22 | 10.53 | 1.65 |
| n-butene | 70.18 | 61.80 | 0.00 | 0.00 | 82.51 | 3.24 | 84.12 | 55.14 | 7.94 | 17.20 |
| butanes | 5.46 | 11.87 | 0.00 | 0.00 | 15.85 | 96.70 | 14.21 | 14.45 | 9.26 | 9.29 |
| C5+ | 0.00 | 0.86 | 0.00 | 0.00 | 1.15 | 0.05 | 1.18 | 4.82 | 0.00 | 71.86 |
| methanol | 0.00 | 0.00 | 100.00 | 0.00 | 0.00 | 0.00 | 0.00 | 0.00 | 0.00 | 0.00 |
| MTBE | 0.00 | 0.00 | 0.00 | 100.00 | 0.00 | 0.00 | 0.00 | 0.00 | 0.00 | 0.00 |
|  | 100.00 | 100.00 | 100.00 | 100.00 | 100.00 | 100.00 | 100.00 | 100.00 | 100.00 | 100.00 |

EXAMPLE 2

With reference to FIG. 2 and the relative Table 2 showing process quantities for a capacity of 1000 kg/a, the isomerization section is fed with a C$_4$ hydrocarbon stream (1) from an existing MTBE plant, not shown in the figure. This stream, with a flow rate of 113.6 g/h and containing about 11% of butanes, is added to the stream (7) from the butane separation unit, and fed to the isomerization section where the n-butenes are converted to isobutene. The by-products (streams 9 and 9') are eliminated and the remaining olefinic stream (8) is fed to the etherification section where, by adding 45.5 g/h of methanol, 125 g/h of MTBE (4) are produced. A part (25%) of the residual stream (5) is fed to the separation unit (100 cc of zeolite X as in Example 1) from which 11.5 g/h of 96.7% butanes are bled off (desorbent n-hexane; flow rate about 120 g/h). The stream (7), mixed with the by-passed stream, is added to the feed stream (1) and fed to the isomerization section.

TABLE 2

MATERIAL BALANCE (g/h)

|  | 1 | 3 | 4 | 5 | 6 | 7 | 8 | 9 | 9' | 10 |
|---|---|---|---|---|---|---|---|---|---|---|
| C3− | 0.2 |  |  | 0.9 | 0.0 | 0.9 | 0.9 | 3.7 | 0.0 | 1.2 |
| isobutene | 0.2 |  |  | 0.4 | 0.0 | 0.4 | 79.9 | 0.5 | 0.3 | 0.6 |
| n-butene | 100.0 |  |  | 177.7 | 0.4 | 177.3 | 177.7 | 0.4 | 2.9 | 277.3 |
| butanes | 12.9 |  |  | 70.0 | 11.1 | 58.8 | 70.0 | 0.6 | 1.9 | 71.7 |
| C5+ | 0.3 |  |  | 4.0 | 0.0 | 4.0 | 4.0 | 0.0 | 12.3 | 4.3 |
| methanol | 0.0 | 45.5 |  |  |  |  |  |  |  |  |
| MTBE | 0.0 |  | 125.0 |  |  |  |  |  |  |  |
| TOTAL | 113.6 | 45.5 | 125.0 | 252.9 | 11.5 | 241.4 | 332.5 | 5.2 | 17.3 | 355.0 |
| Tot. OLEF | 100.2 | 0.0 | 0.0 | 178.1 | 0.4 | 177.7 | 257.6 | 0.9 | 3.1 | 277.9 |

|  | wt % | wt % | wt % | wt % | wt % | wt % | wt % | wt % | wt % | wt % |
|---|---|---|---|---|---|---|---|---|---|---|
| C3− | 0.20 | 0.00 | 0.00 | 0.37 | 0.02 | 0.38 | 1.31 | 70.62 | 0.00 | 0.33 |
| isobutene | 0.16 | 0.00 | 0.00 | 0.16 | 0.01 | 0.17 | 22.75 | 10.20 | 1.61 | 0.16 |
| n-butene | 88.03 | 0.00 | 0.00 | 70.24 | 3.20 | 73.44 | 50.96 | 7.57 | 16.49 | 78.11 |
| butanes | 11.35 | 0.00 | 0.00 | 27.66 | 96.70 | 24.37 | 20.43 | 11.61 | 11.18 | 20.20 |
| C5+ | 0.26 | 0.00 | 0.00 | 1.57 | 0.07 | 1.64 | 4.57 | 0.00 | 70.72 | 1.20 |
| methanol | 0.00 | 100.00 | 0.00 | 0.00 | 0.00 | 0.00 | 0.00 | 0.00 | 0.00 | 0.00 |
| MTBE | 0.00 | 0.00 | 100.00 | 0.00 | 0.00 | 0.00 | 0.00 | 0.00 | 0.00 | 0.00 |
|  | 100.00 | 100.00 | 100.00 | 100.00 | 100.00 | 100.00 | 100.00 | 100.00 | 100.00 | 100.00 |

EXAMPLE 3

With reference to the scheme of FIG. 3 and the relative Table 3 an MTBE production reactor is fed with the C$_4$ hydrocarbon stream of Example 1 (1), but at a rate of 100 g/h, in combination with the recycle stream (7) at a rate of about 226 g/h.

45.7 g/h of methanol are also fed to the reactor (line 3).

The MTBE production (4) is 125.7 g/h with an isobutene conversion of 99.5%.

246.1 g/h of a residual C₄ fraction containing about 19 wt % of aliphatic hydrocarbons is discharged from the synthesis section A via (10). This stream is fed to the isomerization unit C. After eliminating the by-products (9) and (9'), the residual stream (5) is fed to the separation unit B. About 84% of this fraction is by-passed, the remainder being fed to the separation section operating at 130° C. and 4 bar pressure. 100 cc of zeolite X are used as adsorbent, as in Example 1. A stream (6) is bled off consisting essentially of 4.4 g/h of aliphatic hydrocarbons with a paraffin content of about 96.7%.

The stream (7) is added to the stream (1) and then fed to the etherification section.

100 cc of zeolite X in the form of 1/16" extruded pellets are used as adsorbent, n-hexane in the vapour phase (about 120 g/h) being used as desorbent for the adsorbed olefins. After separating the desorbent by distillation, a stream (5") consisting essentially of 5.2 g/h of aliphatic hydrocarbons with a paraffin content of about 96.2% (96.7% of the sum of butenes+butanes) is bled off. In stream (6) the aliphatic hydrocarbon content is reduced to 8.8 wt % after separating the desorbent by distillation.

The stream (6) is fed to the butadiene hydrogenation section H in which the butadiene is converted almost totally into linear butenes, a small part being converted into isobu-

TABLE 3

| | MATERIAL BALANCE (g/h) | | | | | | | | | |
|---|---|---|---|---|---|---|---|---|---|---|
| | 1 | 2 | 3 | 4 | 5 | 6 | 7 | 9 | 9' | 10 |
| C3− | 0.10 | 0.74 | | | 0.64 | 0.00 | 0.64 | 2.55 | 0.00 | 0.74 |
| isobutene | 24.26 | 80.39 | | | 56.17 | 0.04 | 56.13 | 0.38 | 0.20 | 0.40 |
| n-butene | 70.18 | 195.35 | | | 125.27 | 0.10 | 125.17 | 0.28 | 2.01 | 195.35 |
| butanes | 5.46 | 46.91 | | | 45.74 | 4.29 | 41.45 | 0.41 | 1.32 | 46.91 |
| C5+ | 0.00 | 2.73 | | | 2.73 | 0.00 | 2.73 | 0.00 | 8.43 | 2.73 |
| methanol | 0.00 | | 45.71 | | | | | | | |
| MTBE | 0.00 | | | 125.69 | | | | | | |
| TOTAL | 100.00 | 326.12 | 45.71 | 125.69 | 230.55 | 4.43 | 226.12 | 3.62 | 11.96 | 246.13 |
| Tot. OLEF | 94.44 | 275.74 | 0.0 | 0.00 | 195.75 | 0.14 | 181.30 | 0.66 | 2.21 | 195.75 |
| | wt % | wt % | wt % | wt % | wt % | wt % | wt % | wt % | wt % | wt % |
| C3− | 0.10 | 0.23 | 0.00 | 0.00 | 0.28 | 0.01 | 0.28 | 70.52 | 0.00 | 0.30 |
| isobutene | 24.26 | 24.65 | 0.00 | 0.00 | 24.36 | 1.00 | 24.82 | 10.39 | 1.64 | 0.16 |
| n-butene | 70.18 | 59.90 | 0.00 | 0.00 | 54.34 | 2.24 | 55.36 | 7.74 | 16.84 | 79.37 |
| butanes | 5.46 | 14.39 | 0.00 | 0.00 | 19.84 | 96.70 | 18.33 | 11.36 | 11.04 | 19.06 |
| C5+ | 0.00 | 0.84 | 0.00 | 0.00 | 1.18 | 0.05 | 1.21 | 0.00 | 70.48 | 1.11 |
| methanol | 0.00 | 0.00 | 100.00 | 0.00 | 0.00 | 0.00 | 0.00 | 0.00 | 0.00 | 0.00 |
| MTBE | 0.00 | 0.00 | 0.00 | 100.00 | 0.00 | 0.00 | 0.00 | 0.00 | 0.00 | 0.00 |
| | 100.00 | 100.00 | 100.00 | 100.00 | 100.00 | 100.00 | 100.00 | 100.00 | 100.00 | 100.00 |

EXAMPLE 4

With reference to the scheme of FIG. 4 and the accompanying Table 4 showing the process quantities for a capacity of about 100 g/h, an integrated cycle for the simultaneous production of MTBE and 1-butene is fed with a C₄ hydrocarbon stream (1) at a rate of 100.0 g/h and with the following composition:

| | wt % |
|---|---|
| C3− | 0.45 |
| isobutene | 23.57 |
| 1-butene | 36.67 |
| 2-butenes | 34.13 |
| isobutane | 1.50 |
| n-butane | 2.85 |
| butadiene | 0.74 |
| C5+ | 0.10 | in combination with the recycle stream (10) at a rate of 147.8 g/h.

36.2 g of methanol are also fed (line 3) to the reactor A. MTBE production (4) is 98.4 g/h, equivalent to an isobutene conversion of 99.9%.

185.5 g/h of residual C₄ fraction containing about 11 wt % of aliphatic hydrocarbons are discharged from the synthesis section A via (5). About 60% of this fraction is by-passed, the remainder being fed to the molecular sieve separation section operating at 130° C. and 4 bar pressure.

tane. The hydrogenated stream (7) is fed to the 1-butene recovery section R.

In the examined configuration of FIG. 4, the stream (7) is fed to a first distillation column R', from the top of which 30.8 g/h of the isobutane stream (7") is obtained consisting essentially of all the isobutane and all the C₃ hydrocarbons contained in stream (7) plus 1-butene. In the considered configuration the stream (7") is fed to the skeleton isomerization section C.

The stream (8') (148.2 g/h), substantially free from isobutane, is fed to the column R" from which 18.45 g/h of 1-butene are obtained as top product with a purity exceeding 99% (8). The stream (8") (129.75 g/h) is added to the stream (7") to form the stream (9) (160.5 g/h). This latter stream is fed to the isomerization section C in which the n-butenes are converted to isobutene and other by-products generally falling within the C₃- and C₅+ categories. These by-products are eliminated (streams 9 and 9') and the resultant fraction (10) is recycled to the MTBE synthesis section.

TABLE 4

MATERIAL BALANCE

|  | 1 g/h | 2 g/h | 3 g/h | 4 g/h | 5 g/h | 5' g/h | 5" g/h | 6 g/h | 6' g/h | 6" g/h |
|---|---|---|---|---|---|---|---|---|---|---|
| light BCs | 0.02 | 0.02 | 0.00 | 0.00 | 0.02 | 0.01 | 0.00 | 0.02 | 0.10 | 0.05 |
| C3 | 0.43 | 0.58 | 0.00 | 0.00 | 0.58 | 0.35 | 0.00 | 0.58 | 0.00 | 0.03 |
| isobutane | 1.50 | 6.29 | 0.00 | 0.00 | 6.29 | 3.77 | 1.51 | 4.78 | 0.00 | 0.07 |
| isobutene | 23.57 | 62.54 | 0.00 | 0.00 | 0.06 | 0.04 | 0.00 | 0.06 | 0.00 | 0.00 |
| 1-butene | 36.67 | 62.16 | 0.00 | 0.00 | 62.16 | 37.30 | 0.07 | 62.10 | 0.00 | 0.59 |
| dienes | 0.74 | 0.77 | 0.00 | 0.00 | 6.77 | 0.46 | 0.00 | 0.77 | 0.00 | 0.00 |
| n-butane | 2.85 | 14.70 | 0.00 | 0.02 | 14.68 | 8.81 | 3.52 | 11.16 | 0.00 | 0.09 |
| 2-butenes | 34.13 | 98.49 | 0.00 | 0.06 | 98.43 | 59.06 | 0.11 | 98.32 | 0.00 | 0.59 |
| heavy BCs | 0.10 | 2.33 | 0.00 | 0.09 | 2.24 | 1.34 | 0.02 | 2.27 | 0.00 | 0.00 |
| methanol | 0.00 | 0.00 | 36.22 | 0.10 | 0.41 | 0.24 | 0.00 | 0.36 | 0.00 | 0.08 |
| MTBE | 0.00 | 0.00 | 0.00 | 98.15 | 0.00 | 0.00 | 0.00 | 0.00 | 0.00 | 0.00 |
| TOTAL | 100.00 | 247.88 | 36.22 | 98.42 | 185.64 | 111.39 | 5.23 | 180.42 | 0.10 | 1.50 |
| Tot. OLEF | 94.37 | 223.19 | 0.00 | 0.00 | 160.65 | 96.39 | 0.17 | 160.48 | 0.00 | 1.18 |
|  | wt % | wt % | wt % | wt % | wt % | wt % | wt % | wt % | wt % | wt % |
| light BCs | 0.02 | 0.01 | 0.00 | 0.00 | 0.01 | 0.01 | 0.00 | 0.01 | 100.00 | 3.04 |
| C3 | 0.43 | 0.23 | 0.00 | 0.00 | 0.31 | 0.31 | 0.03 | 0.32 | 0.00 | 2.18 |
| isobutane | 1.50 | 2.54 | 0.00 | 0.00 | 3.39 | 3.39 | 28.86 | 2.65 | 0.00 | 4.45 |
| isobutene | 23.57 | 25.23 | 0.00 | 0.00 | 0.03 | 0.03 | 0.00 | 0.03 | 0.00 | 0.04 |
| 1-butene | 36.67 | 25.08 | 0.00 | 0.00 | 33.49 | 33.49 | 1.25 | 34.42 | 0.00 | 39.53 |
| dienes | 0.74 | 0.31 | 0.00 | 0.00 | 0.41 | 0.41 | 0.00 | 0.43 | 0.00 | 0.01 |
| n-butane | 2.85 | 5.93 | 0.00 | 0.02 | 7.91 | 7.91 | 67.35 | 6.19 | 0.00 | 6.22 |
| 2-butenes | 34.13 | 39.73 | 0.00 | 0.06 | 53.02 | 53.02 | 2.03 | 54.50 | 0.00 | 39.10 |
| heavy BCs | 0.10 | 0.94 | 0.00 | 0.10 | 1.21 | 1.21 | 0.47 | 1.26 | 0.00 | 0.03 |
| methanol | 0.00 | 0.00 | 100.00 | 0.10 | 0.22 | 0.22 | 0.00 | 0.20 | 0.00 | 5.40 |
| MTBE | 0.00 | 0.00 | 0.00 | 99.72 | 0.00 | 0.00 | 0.00 | 0.00 | 0.00 | 0.00 |
| TOTAL | 100.00 | 100.00 | 100.00 | 100.00 | 100.00 | 100.00 | 100.00 | 100.00 | 100.00 | 100.00 |
| Tot. OLEF | 94.37 | 90.04 | 0.00 | 0.06 | 86.54 | 86.54 | 3.28 | 88.95 | 0.00 | 78.67 |

|  | 7 g/h | 7' g/h | 8 g/h | 8' g/h | 8" g/h | 9 g/h | 9' g/h | 9" g/h | 10 g/h |
|---|---|---|---|---|---|---|---|---|---|
| light BCs | 0.02 | 0.02 | 0.00 | 0.00 | 0.00 | 0.35 | 0.36 | 0.00 | 0.00 |
| C3 | 0.55 | 0.55 | 0.00 | 0.00 | 0.00 | 2.01 | 1.88 | 0.00 | 0.15 |
| isobutane | 4.71 | 4.70 | 0.01 | 0.02 | 0.00 | 4.84 | 0.08 | 0.01 | 4.79 |
| isobutene | 0.06 | 0.02 | 0.02 | 0.04 | 0.02 | 39.17 | 0.27 | 0.29 | 38.97 |
| 1-butene | 60.70 | 15.25 | 18.38 | 45.45 | 27.07 | 25.64 | 0.15 | 0.23 | 25.49 |
| dienes | 0.01 | 0.00 | 0.00 | 0.01 | 0.00 | 0.03 | 0.00 | 0.00 | 0.03 |
| n-butane | 12.00 | 1.46 | 0.03 | 10.54 | 10.50 | 12.03 | 0.03 | 0.26 | 11.85 |
| 2-butenes | 98.43 | 8.54 | 0.00 | 89.89 | 89.89 | 66.25 | 0.10 | 2.40 | 64.36 |
| heavy BCs | 2.27 | 0.01 | 0.00 | 2.26 | 2.26 | 8.63 | 0.00 | 6.48 | 2.23 |
| methanol | 0.28 | 0.28 | 0.00 | 0.00 | 0.00 | 1.61 | 0.10 | 0.00 | 0.00 |
| MTBE | 0.00 | 0.00 | 0.00 | 0.00 | 0.00 | 0.00 | 0.00 | 0.00 | 0.00 |
| TOTAL | 179.02 | 30.81 | 18.45 | 148.20 | 129.75 | 160.56 | 2.96 | 9.69 | 147.88 |
| Tot. OLEF | 159.18 | 23.80 | 18.40 | 135.38 | 116.98 | 131.05 | 0.52 | 2.93 | 128.82 |
|  | wt % | wt % | wt % | wt % | wt % | wt % | wt % | wt % | wt % |
| light BCs | 0.01 | 0.05 | 0.00 | 0.00 | 0.00 | 0.22 | 12.05 | 0.00 | 0.00 |
| C3 | 0.31 | 1.77 | 0.00 | 0.00 | 0.00 | 1.25 | 63.37 | 0.00 | 0.10 |
| isobutane | 2.63 | 15.24 | 0.08 | 0.01 | 0.00 | 3.01 | 2.56 | 0.15 | 3.24 |
| isobutene | 0.03 | 0.06 | 0.12 | 0.03 | 0.02 | 24.40 | 9.17 | 3.04 | 26.35 |
| 1-butene | 33.91 | 49.48 | 99.58 | 30.67 | 28.87 | 15.97 | 5.06 | 2.41 | 17.24 |
| dienes | 0.00 | 0.01 | 0.01 | 0.00 | 0.00 | 0.02 | 0.01 | 0.00 | 0.02 |
| n-butane | 6.70 | 4.75 | 0.18 | 7.11 | 0.10 | 7.49 | 1.01 | 2.71 | 8.02 |
| 2-butenes | 54.98 | 27.70 | 0.01 | 60.65 | 69.28 | 41.26 | 3.49 | 24.80 | 43.52 |
| heavy BCs | 1.27 | 0.04 | 0.00 | 1.52 | 1.74 | 5.38 | 0.00 | 66.89 | 1.51 |
| methanol | 0.16 | 0.90 | 0.01 | 0.00 | 0.00 | 1.00 | 3.28 | 0.00 | 0.20 |
| MTBE | 0.00 | 0.00 | 0.00 | 0.00 | 0.00 | 0.00 | 0.00 | 0.00 | 0.00 |
| TOTAL | 100.00 | 100.00 | 100.00 | 100.00 | 100.00 | 100.00 | 100.00 | 100.00 | 100.00 |
| Tot. OLEF | 68.92 | 77.24 | 99.71 | 91.36 | 90.16 | 81.62 | 17.72 | 30.25 | 87.11 |

EXAMPLE 5

Samples of type X zeolite in the form of 1/16" pellets are heated in a muffle furnace to 400° C. for 5 hours in a nitrogen stream. 4 g of zeolite treated in this manner are loaded into an AISI 316 steel column of length about 25 cm which is housed in an oven and raised to a temperature of 90° C.

When this temperature is reached a n-hexane vapour stream is passed through the column for about 1000 seconds to saturate the active zeolite sites. A $C_4$ vapour phase stream is then passed through at a rate of 7.6 l/h.

The $C_4$ stream has the following composition:

|  | wt % |
|---|---|
| isobutane | 3.8 |
| isobutene | 4.4 |
| n-butane | 11.2 |
| n-butenes | 80.0 |
| 1,3-butadiene | 0.6 |

The $C_4$ stream is passed through the column for about 1100 seconds. The flow is then stopped and a vapour phase n-hexane stream is then fed at a rate of 0.6 cc/min for about 1800 seconds.

The effluent from the system is condensed in a glass heat exchanged at $-15°$ C.

The recovered mixture consists of the sum of the adsorbed $C_4$ quantity and the quantity contained in the system volume not occupied by the zeolite.

The $C_4$ mixture recovered at the column exit has the following composition:

|  | wt % |
|---|---|
| isobutane | 1.15 |
| isobutene | 4.78 |
| n-butane | 3.46 |
| n-butenes | 88.77 |
| 1,3-butadiene | 1.84 |

The experimental data and gas chromatography analysis of the condensed liquid show the following system selectivities.

| isobutene/n-butane | 3.60 |
|---|---|
| 1-butene/n-butane | 3.70 |
| t-2-butene/n-butane | 2.76 |
| c-2-butene/n-butane | 4.13 |

The system selectivity $S_i$ is defined as the following ratio:

$$Si = \frac{A_o/A_i}{R_o/R_i}$$

where:

A and R are the mole fraction of the $C_4$ in the feed and in the solution recovered respectively;

i and o are the generic component and reference component (n-butane) respectively.

EXAMPLE 6

The procedure of Example 4 is followed except that a Y zeolite is used instead of an X zeolite. The flow rate of the $C_4$ stream is 0.5 cc/min.

The $C_4$ mixture recovered at the column exit has the following composition:

|  | wt % |
|---|---|
| isobutane | 1.00 |
| isobutene | 6.44 |
| n-butane | 3.87 |
| n-butenes | 87.38 |
| 1,3-butadiene | 1.31 |

The experimental data and the gas chromatography analysis of the condensed liquid show the following system selectivities.

| isobutene/n-butane | 4.33 |
|---|---|
| 1-butene/n-butane | 3.00 |
| t-2-butene/n-butane | 3.22 |
| c-2-butene/n-butane | 5.30 |

EXAMPLE 7 (Comparative)

The procedure of Example 5 is followed except that the $C_4$ mixture and the hexane are used in the liquid phase. To achieve this, the operating pressure within the system is 14 bar.

The $C_4$ mixture recovered at the column exit has the following composition:

|  | wt % |
|---|---|
| isobutane | 3.63 |
| isobutene | 4.45 |
| n-butane | 10.66 |
| n-butenes | 80.62 |
| 1,3-butadiene | 0.64 |

The experimental data and the gas chromatography analysis of the condensed liquid show the following system selectivities.

| isobutene/n-butane | 1.08 |
|---|---|
| 1-butene/n-butace | 1.05 |
| t-2-butene/n-butane | 1.06 |
| c-2-butene/n-butane | 1.11 |

We claim:

1. An integrated process for producing alkyl tert-butyl ethers comprising:

a) feeding a $C_4$ hydrocarbon stream, consisting essentially of isobutene, linear butenes and butanes, to an alkyl tert-butyl ether synthesis section together with an aliphatic alcohol stream;

b) separating the ether produced and any unreacted alcohol from the hydrocarbon stream;

c) feeding the remaining hydrocarbon stream, or fraction thereof, in the vapour phase, to a molecular sieve separation section for separating the butanes from the butenes and recovering the butenes;

d) feeding the hydrocarbon stream containing the recovered butenes, together with the possible fraction not fed to stage c), to a skeleton isomerization section for converting the linear butenes to isobutene;

e) recycling the isomerized stream to the alkyl tert-butyl ether synthesis reactor after mixing with the $C_4$ hydrocarbon feedstock stream.

2. An integrated process for producing alkyl tert-butyl ethers comprising:
 a) feeding a $C_4$ hydrocarbon stream, consisting essentially of isobutene, linear butenes and butanes, to an alkyl tert-butyl ether synthesis section together with an aliphatic alcohol stream;
 b) separating the ether produced and any unreacted alcohol from the hydrocarbon stream;
 c) feeding the remaining hydrocarbon stream to a butene skeleton isomerization section for converting the linear butenes to isobutene;
 d) feeding the isomerized hydrocarbon stream leaving C, or fraction thereof, in the vapour phase, to a molecular sieve separation section for separating the butanes from the butenes and recovering the butenes;
 e) recycling the isomerized stream containing the recovered butenes, together with the possible fraction not fed to stage d), to the alkyl tert-butyl ether synthesis reactor after mixing with the $C_4$ hydrocarbon feedstock stream.

3. A process as claimed in claim 1 or 2, wherein the $C_4$ hydrocarbon stream is substantially free from isobutene and is fed directly to the isomerization section.

4. An integrated process for simultaneously producing alkyl tert-butyl ethers and 1-butene comprising:
 a) feeding a fresh $C_4$ hydrocarbon feedstock stream, consisting essentially of isobutene, linear butenes and butanes, plus a recycle stream containing possible traces of butadiene, to an alkyl tert-butyl ether synthesis section together with an aliphatic alcohol stream;
 b) separating the ether produced and any unreacted alcohol from the hydrocarbon stream;
 c) feeding the remaining hydrocarbon stream, or a fraction thereof (first by-pass), in the vapour phase to a molecular sieve separation section for separating the paraffins from the butenes, recovering the butenes and bleeding off the paraffins;
 d) feeding the thus treated hydrocarbon stream to a butadiene selective hydrogenation unit;
 e) feeding the hydrocarbon stream from the butadiene hydrogenation unit, or a fraction thereof (second by-pass), to a 1-butene separation unit to obtain a 1-butene stream of purity exceeding 99%, a stream consisting essentially of residual isobutane and 1-butene (isobutane stream) and a stream consisting essentially of 2-butenes, 1-butene and residual n-butane (butene stream);
 f) feeding the butene stream of stage e) to a skeleton isomerization section for converting the linear butenes to isobutene;
 g) feeding the isobutane stream of stage e) either to the molecular sieve separation section or directly to the isomerization section;
 h) recycling the isomerized stream to the tert-butyl alkyl ether synthesis reactor after mixing with the $C_4$ hydrocarbon feedstock stream.

5. A process as claimed in claim 4, wherein the $C_4$ hydrocarbon feedstock stream contains traces of butadiene and is practically free from isobutene, and is fed directly upstream of the butadiene selective hydrogenation unit and downstream of the molecular sieve separation section.

6. A process as claimed in claim 4, wherein the butadiene selective hydrogenation unit is positioned upstream of the molecular sieve separation section and upstream of the first by-pass.

7. A process as claimed in claim 6, wherein the $C_4$ hydrocarbon feedstock stream contains traces of butadiene and is practically free from isobutene, and is fed upstream of the selective hydrogenation section and downstream of the etherification section.

8. A process as claimed in claim 4, wherein the 1-butene is separated by distillation, extractive distillation or adsorption on molecular sieves.

9. A process as claimed in claim 8, wherein the 1-butene is separated at high purity by two distillation columns arranged in series, in the first of which a mixture consisting of essentially of 1-butene and isobutane (isobutane stream) is separated as top product, and in the second of which, fed with the bottom product of the first, 1-butene is obtained as top product with a purity exceeding 99%, the bottom product being a stream rich in residual n-butane, cis and trans 2-butene and traces of 1-butene (butene stream).

10. A process as claimed in claim 8, wherein the 1-butene is separated at high purity by two distillation columns arranged in series, from the first of which the butene stream is discharged as bottom product, from the second of which the high purity 1-butene is obtained as bottom product, the isobutane stream being discharged as top product.

11. A process as claimed in claim 1, wherein the aliphatic alcohol is methyl or ethyl alcohol.

12. A process as claimed in claim 1, wherein a hydrocarbon stream fraction exceeding 5% of the total available stream is fed to the molecular sieve separation section.

13. A process as claimed in claim 1, wherein the molecular sieves are of zeolite type able to present selectivity towards the olefin double bond and of general formula (I):

$$(Cat_{2/n}O)_x Me_2O_3 (SiO_2)_y \qquad (I)$$

where:
 Cat represents a cation of valency "n" interchangeable with calcium (Ca), such as sodium, lithium, potassium, magnesium etc;
 x is a number between 0.7 and 1.5;
 Me represents boron or aluminium; and
 y is a number between 0.8 and 200, preferably between 1.3 and 4.

14. A process as claimed in claim 13, wherein the molecular sieves are zeolites of X or Y type with a particle size of between 0.1 and 3 mm.

15. A process as claimed in claim 1, wherein the zeolite olefin/paraffin selectivity ratio is between 3 and 12.

16. A process as claimed in claim 1, wherein the separation is conducted in the vapour phase at a temperature of between 20° and 180° C. and a pressure of between 1 and 10 bar.

17. A process as claimed in claim 1, wherein the butenes are recovered by eluting the olefins adsorbed on the molecular sieves with aliphatic hydrocarbons followed by rectification of the mixture obtained.

* * * * *